(12) United States Patent
Asher

(10) Patent No.: US 7,591,190 B2
(45) Date of Patent: Sep. 22, 2009

(54) TEST STAND

(75) Inventor: Michael J. Asher, Cincinnati, OH (US)

(73) Assignee: American Fabricating, LLC, Cincinnati, OH (US)

( * ) Notice: Subject to any disclaimer, the term of this patent is extended or adjusted under 35 U.S.C. 154(b) by 41 days.

(21) Appl. No.: 11/276,363

(22) Filed: Feb. 27, 2006

(65) Prior Publication Data

US 2007/0199387 A1  Aug. 30, 2007

(51) Int. Cl.
*G01N 3/02* (2006.01)
(52) U.S. Cl. .......................................................... 73/856
(58) Field of Classification Search .................... 73/856
See application file for complete search history.

(56) References Cited

U.S. PATENT DOCUMENTS

| | | | | |
|---|---|---|---|---|
| 2,560,500 | A | * | 7/1951 | Reginald ..................... 187/362 |
| 2,763,149 | A | | 9/1956 | Long et al. |
| 2,825,477 | A | * | 3/1958 | Ross ............................ 29/559 |
| 3,719,295 | A | * | 3/1973 | Grace .......................... 414/635 |
| 3,722,267 | A | | 3/1973 | Gordon |
| 3,726,431 | A | * | 4/1973 | Botkin ........................ 220/1.5 |
| 3,768,261 | A | * | 10/1973 | Gordon ........................ 60/328 |
| 3,879,991 | A | | 4/1975 | Ristow et al. |
| 3,958,443 | A | | 5/1976 | Berrettini |
| 4,223,554 | A | | 9/1980 | Ulbing |
| 4,509,377 | A | * | 4/1985 | Mentzell et al. .......... 73/862.56 |
| 5,005,424 | A | | 4/1991 | Markowski |
| 5,333,757 | A | * | 8/1994 | Volk et al. ..................... 222/94 |
| 5,417,406 | A | * | 5/1995 | Fanchier, Jr. ................. 254/199 |
| 5,431,060 | A | | 7/1995 | Lauren |
| 5,499,530 | A | | 3/1996 | Vondell et al. |
| 5,677,494 | A | | 10/1997 | Keener et al. |
| 5,948,994 | A | | 9/1999 | Jen et al. |
| 6,622,571 | B2 | | 9/2003 | Chen |
| 6,912,916 | B1 | | 7/2005 | Joubert |
| 6,976,396 | B2 | | 12/2005 | Roe et al. |

OTHER PUBLICATIONS

Coffing Hoists, CB-16 Hoist Test Stand, The Hydraulic, Hand Operated Test Stand Value-Priced—Tests Hoist Capacity to 12 Tons, 2000, Coffing Hoists, Wadesboro, NC.

* cited by examiner

*Primary Examiner*—Lisa M Caputo
*Assistant Examiner*—Octavia Davis
(74) *Attorney, Agent, or Firm*—David E. Pritchard

(57) ABSTRACT

A test stand (10) for testing hoists (16) includes a test frame (12) and a tensioning device (14) to apply a tensile load to the hoist (16) being tested. The hoist (16) is connected to the test stand (10) at two connection points (26, 28) to which the tensioning device (14) applies a tensile load. Support legs (18, 20) are mounted to the test frame (12) for orienting the test frame (12) in either a generally vertical orientation or in a generally horizontal orientation to facilitate attachment of heavy hoists (16) for testing. Test frame (12) mounted receptacles (44) cooperate with forklift blades (122) for facilitating the transport of the test stand (10).

23 Claims, 4 Drawing Sheets

TEST STAND

FIELD OF THE INVENTION

The present invention relates to test stands for testing hoists.

DESCRIPTION OF PRIOR ART

Chain hoists typically include a hoist with a hook for suspending the hoist and a chain depending from the hoist with a hook at a lower end for attachment to a load or a fixed member. It is desirable to provide a test stand for testing the rated load of such a hoist.

A typical test stand for testing a chain hoist includes an upright rectangular frame having two elongated support legs mounted to hold the frame erect or generally vertical relative to the ground. A hydraulic cylinder is oriented at a top frame member and a hydraulic pump is used to selectively apply the tensile force to a chain hoist mounted between a piston of the cylinder and a lower frame member. One such test stand is offered by the Coffing Hoists Company of Wadesboro, N.C.

In some situations, the chain hoist to be tested is quite heavy. An operator thus has to find a way to lift the heavy chain hoist to hook or connect it to the test stand, and especially to the upper connection point with the cylinder which may be several feet off the ground. Typically, that is an intensive manual effort and presents risks of injury to the operator. One proposal to deal with heavy chain hoists is shown in U.S. Pat. No. 6,912,916 in which there is a jig at the upper end of the test stand that can be used with another hoist to lift the chain hoist to be tested. That presents certain drawbacks as well, not only in the additional complexity of the device, but also in shifting the heavy device from the jig to the connection point on the piston.

It is helpful if test stands can be moved around the factory, for example. Many test stands are unwieldy so movement, even with a forklift, can present certain risks. One proposal has been to put the test stand on wheels. But that then leaves open the risk that the test stand may not hold still during use.

SUMMARY OF THE INVENTION

The present invention provides a test stand that in one aspect is adapted for easy use with heavy hoists, and, in another aspect, is more easily moved about but is stable during use. To that end, and in accordance with the principles of the present invention, the test stand frame is provided not only with the pair of support legs to hold the frame in a generally vertical orientation, but a second set or pair of transverse support legs are mounted at the top of and extend to one side such as the rear of the frame. These cooperate with the first support legs to hold the frame in a stable, generally horizontally attitude near, but spaced above, the ground when the stand is tilted over. While the test frame may therefore be used in the typical generally vertical orientation, with the provision of the second set of support legs, the frame can be tilted over into a generally horizontal attitude so that both the connection point to the cylinder piston and the connection point to the lower frame member are both near the ground, and generally at the same distance from the surface at which a hoist is laid out. The ends of the hoist, even of a heavy chain hoist, can be easily lifted the short distance to the connection points on the stand, and the hoist then tensioned. This tensioning shortens the hoist between the connection points which brings the hoist generally into the plane of the frame for testing.

The first and second pair of support legs, in accordance with one aspect of the invention, support the frame in a stable, generally horizontal position relative to the ground so that the device does not fall over or wobble undesirably. Further, the two pairs of supports hold the frame generally horizontal so the frame is not adversely canted relative to the ground. Having the frame adversely canted relative to the ground can impede the operation of the hydraulic cylinder among other drawbacks.

The test stand of the present invention is thus adapted for easy use with heavy hoists. In accordance with a further aspect of the present invention, the test frame is provided with receptacles which receive forklift blades so as to provide a stable connection with the forklift during movement. When the receptacles are not engaged for lifting by a forklift, the first pair of support legs is sufficient to support the test frame. As a consequence, while the test stand of the present invention could be provided with and moved about on wheels, advantageously, it need not include wheels. Thus, the test stand of the present invention, in another aspect may be easily moved about but is stable during use.

By virtue of the foregoing, there is provided a test stand that in one aspect is adapted for easy use with heavy hoists and, in another aspect, is more easily moved about while stable during use. These and other objects and advantages of the invention shall become apparent from the accompanying drawings and the description thereof.

BRIEF DESCRIPTION OF THE DRAWINGS

The accompanying drawings, which are incorporated in and constitute a part of this specification, illustrate an embodiment of the invention, and together with the general description of the invention given above, and the detailed description of the embodiment given below, serve to explain the principles of the present invention.

DETAILED DESCRIPTION OF THE DRAWINGS

Figure 1:
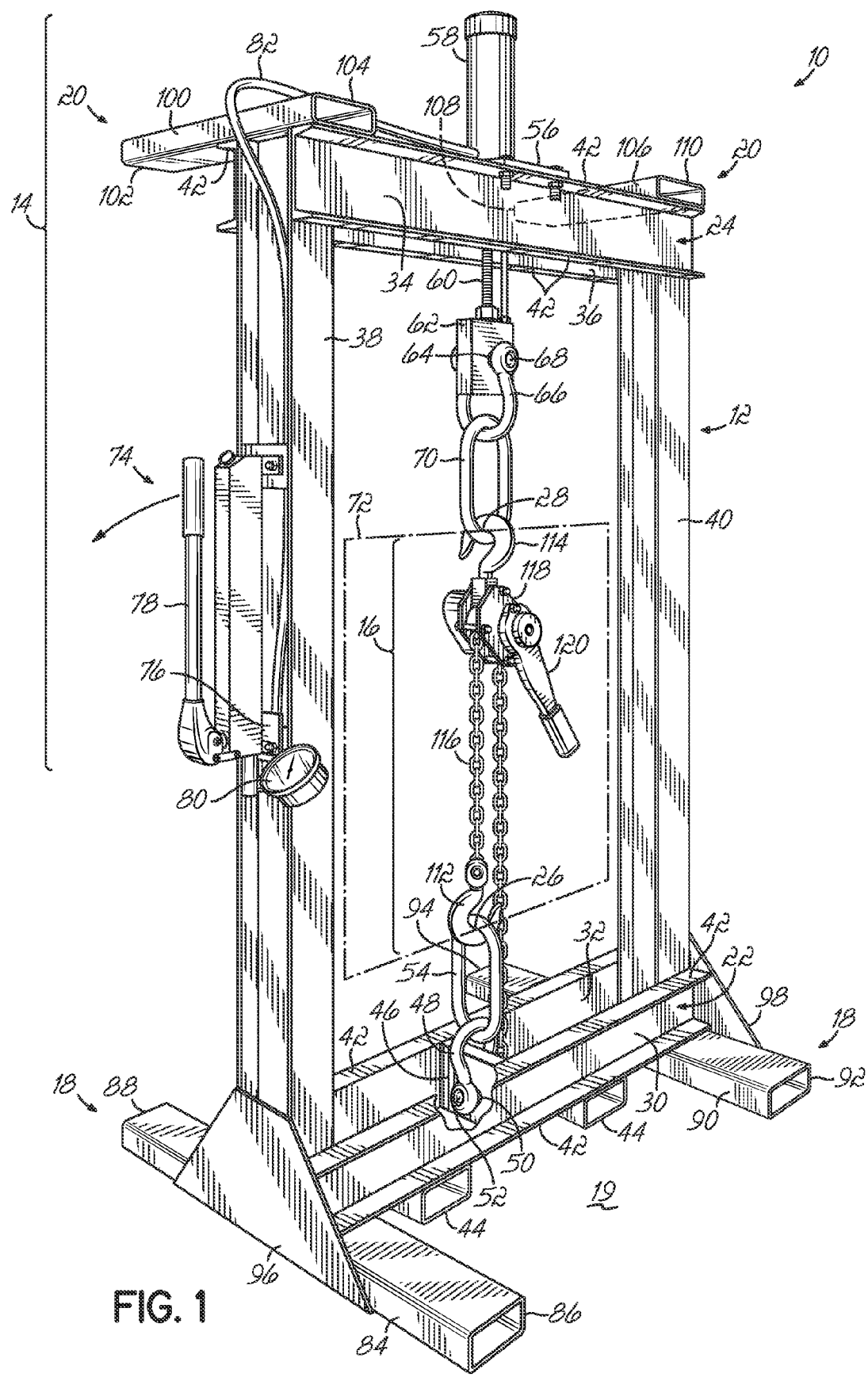
FIG. 1 is a perspective view of one embodiment of the test stand in accordance with the principles of the present invention, illustrating the test frame positioned in the typical generally vertical orientation.

With reference to FIG. 1, one embodiment of a test stand 10 is illustrated. The test stand 10 includes a test frame 12, a tensioning device 14, such as a hydraulic cylinder, to apply a tensile load during the testing of a hoist, such as a chain hoist 16, a first pair of support members 18 to support the test frame 12 in a generally vertical orientation in relation to the ground 19, a second pair of support members 20 which cooperate with the first pair of support members 18 to stably orient the test frame 12 in a generally horizontal orientation in relation to the ground 19. Placing the test frame 12 in a generally horizontal orientation in relation to the ground 19 assists in testing a heavy chain hoist 16 as described below.

The test frame 12 comprises four frame members that define a generally rectangular test frame 12. The four frame members include a first frame member 22 and a spaced apart second frame member 24 comprising bottom and top frame members. These are associated with a first hoist connection point 26 and a second hoist connection point 28, respectively. The first frame member 22 and the second frame member 24 are each advantageously formed of two C-shaped channels that are illustrated as a first pair 30, 32 comprising the first frame member 22 and a second pair 34, 36 comprising the second frame member 24. The second frame member 24 and the first frame member 22 are coupled together using a first side member 38 and a second side member 40 that pass in between the first pair of C-shaped channels 30, 32 and the second pair of C-shaped channels 34, 36 with the flanges 42 of the C-shaped channels 30, 32, 34, 36 flaring outward from side members 38, 40. The side members 38, 40 are I-beams and are spaced approximately 40 inches apart. In the illustrated embodiment, the members 22, 24, 38, 40 are formed of steel and are welded together, however, other embodiments may use other materials and other methods of combining the members 22, 24, 38, 40. The test frame 12 also includes receptacles 44 coupled to the first frame member 22 for purposes to be described in more detail below.

For testing, a chain hoist 16 is mounted in the test frame 12 between the first fixed hoist connection point 26 and the movable second hoist connection point 28 operably coupled to the tensioning device 14. The connection points 26, 28 are simply the locations where the chain hoist 16 is connected to the test frame 12. The first connection point 26 is associated with the first frame member 22 described in more detail. The first pair of C-shaped channels 30, 32 is joined together by welding a rib 46 to the non-flanged portion of the channels 30, 32. A shackle 48 is coupled to the rib 46. The rib 46 has an aperture 50 that a pin 52 of the shackle 48 passes through. The pin 52 of the shackle 48 can rotate in the aperture 50 enabling the shackle 48 to be maneuvered. A weldless endlink 54 provides the first hoist connection point 26 and the weldless endlink 54 is operatively coupled to the shackle 48. Moreover, the second frame member 24 is associated with the second connection point 28 and described in more detail. The second pair of C-shaped channels 34, 36 has a support plate 56 attached using fasteners, such as bolts, that support the tensioning device 14. The tensioning device 14 includes a cylinder 58 that contains a piston (not shown) connected to the rod 60. Movement of the piston (not shown) inside of the cylinder 58 causes the rod 60 to move. The rod 60 is coupled to the plate 62. The plate 62 includes an aperture 64 enabling a second shackle 66 to rotate about a second pin 68 that passes through the aperture 64. Connected to the second shackle 66 is a second weldless endlink 70 that provides the second hoist connection point 28.

In the embodiment illustrated in FIG. 1, the first hoist connection point 26 and the second hoist connection point 28 are generally vertically aligned. The alignment of the first hoist connection point 26 and the second hoist connection point 28 places the points 26, 28 generally as two points of many in a vertical plane 72. A substantial portion of the chain hoist 16 when mounted in the test frame 12 through connection to the first hoist connection point 26 and the second hoist connection point 28 also generally lies in the plane 72. Moreover, the plane 72 is also generally aligned with the test frame 12.

The first and second hoist connection points 26 and 28 respectively are moveable apart tending to apply a tensile load to a chain hoist 16 during testing. The second hoist connection point 28 follows the movement of the piston (not shown) inside of the cylinder 58. The cylinder 58 is adapted to apply a test load of up to 20 tons to the chain hoist 16 during testing.

The tensioning device 14 is controlled using a control device, such as a hand pump 74. The hand pump 74 is affixed to the first side member 38 away from the chain hoist 16. The operator does not have to face or stand close to the chain hoist 16 during testing because of this position. In addition, the hand pump 74 advantageously is much easier to reach. The hand pump 74 includes a base 76 for mounting the hand pump 74 to the first side member 38. The hand pump 74 also includes a lever 78 that can be pulled by the operator to apply incremental amounts of a tensile load to the chain hoist 16 that is being tested. In the illustrated embodiment, the lever 78 generally moves through an arc that is substantially parallel to the plane 72. The amount of force being applied to the chain hoist 16 is determined by looking at the indicator dial 80. Connecting the cylinder 58 and the hand pump 74 is tubing 82 that enable the movement of the lever 78 to alter the pressure in the tubing 82 and concurrently the cylinder 58. Accordingly, the manual movement of the lever 78 results in moving the first and second connection points 26, 28 apart to apply a tensile load to the chain hoist 16 during testing.

The first pair of support members 18 is associated with the test frame 12 to provide support in a generally vertical orientation so the chain hoist 16 can be tested in a generally vertical orientation. The first pair of support members 18 has a first support 84 including a first end 86 and a second end 88 and a second support 90 including a first end 92 and a second end 94. Both the first ends 86, 92 and the second ends 88, 94 lie outside of opposite sides of the plane 72 to provide a stable base for the test stand 10 in the vertical orientation. A first reinforcing plate 96 adapted to increase stability is coupled to the first frame member 22, the first side member 38, and the first base support 84. Similarly, a second reinforcing plate 98 stabilizes the other side of the test frame 12. Therefore, a stable solid base for the test stand 10 is provided in a generally vertical orientation.

Figure 2:
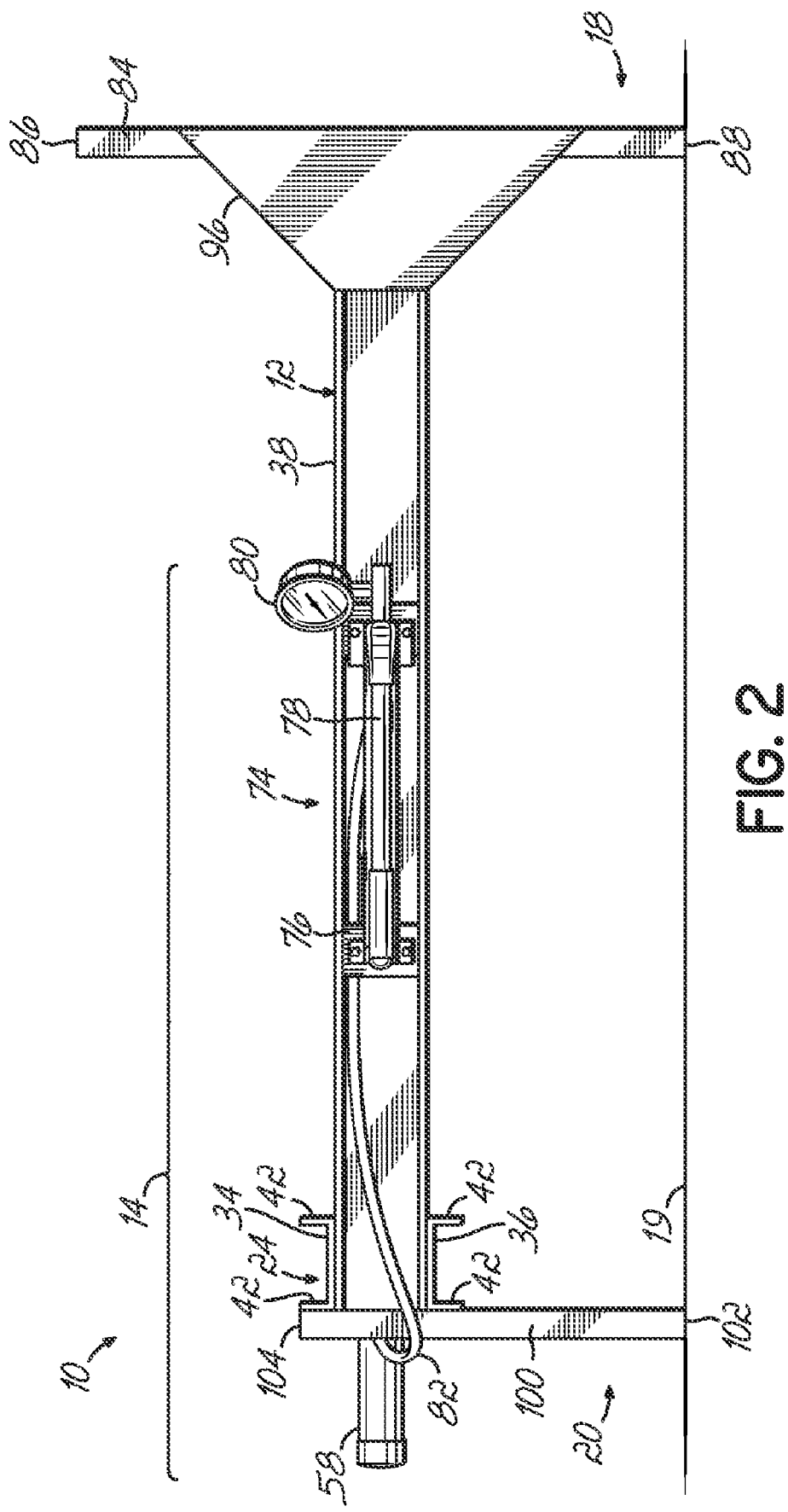
FIG. 2 is a side elevational view of the test stand of FIG. 1 having the test frame positioned in a generally horizontal orientation relative to the ground.

In contrast, FIG. 2 illustrates that the first pair of support members 18 cooperate with the second pair of support members 20 associated with the test frame 12 to support the test frame 12 in a generally horizontal orientation. The generally horizontal orientation facilitates testing of the chain hoist 16 in a generally horizontal orientation. The second pair of support members 20 is associated with the second frame member 24. The second pair of support members 20 has a first support 100 including a first end 102 and a second end 104 and a second support 106 including a first end 108 and a second end 110. The first ends 102, 108 contact the ground 19 when the test stand 10 is in a horizontal position and the second ends 104, 110 are coupled to the second frame member 24. The length of both the first support 100 and the second support 106 is generally identical to the length of the first support 84 and the second support 90 on one side of the plane 72. The first support 100 and the second support 106 preferably do not (but could) extend on the other side of the plane 72 that contains the test frame 12. Thus, the first pair of support members 18 and the second pair of support members 20 cooperate to stably support and balance the test stand 10 in a generally horizontal orientation without having a canted position. In other words, the support members 20 are of such length that when the test frame 12 is tilted over from generally vertical to generally horizontal, it is supported in a generally horizontal orientation, wherein both connection points 26, 28 are disposed approximately at the same vertical level above the ground 19 on which the test frame 12 is disposed.

The chain hoist 16 is tested by the test stand 10. FIG. 1 illustrates that the chain hoist 16 includes a first hook 112 that is coupled to the first hoist connection point 26 and a second hook 114 that is coupled to the second hoist connection point 28. The first hook 112 generally remains stationary throughout the test, as the tensile force tends to pull the first hook 112 and the second hook 114 of the chain hoist 16 apart. The second hook 114 slightly moves towards the cylinder 58 once the tensioning device 14 has begun applying the tensile load. The tendency to separate the first hook 112 and the second hook 114 also places the chain 116 and the chain hoist body 118 under a tensile load. The tensile load determines the strength of the connections between the first hook 112 and the chain 116 and the second hook 114 and the chain 116 along with the strength of the chain 116 alone. Moreover, the gearing system (not shown) inside of the hoist body 118 is stressed to ensure that the gearing system (not shown) cannot slip in a direction opposite to the ratcheting that occurs by moving the ratchet arm 120. The ratchet arm 120 has a release that is also tested to ensure there is no unintentional slip.

Figure 3:
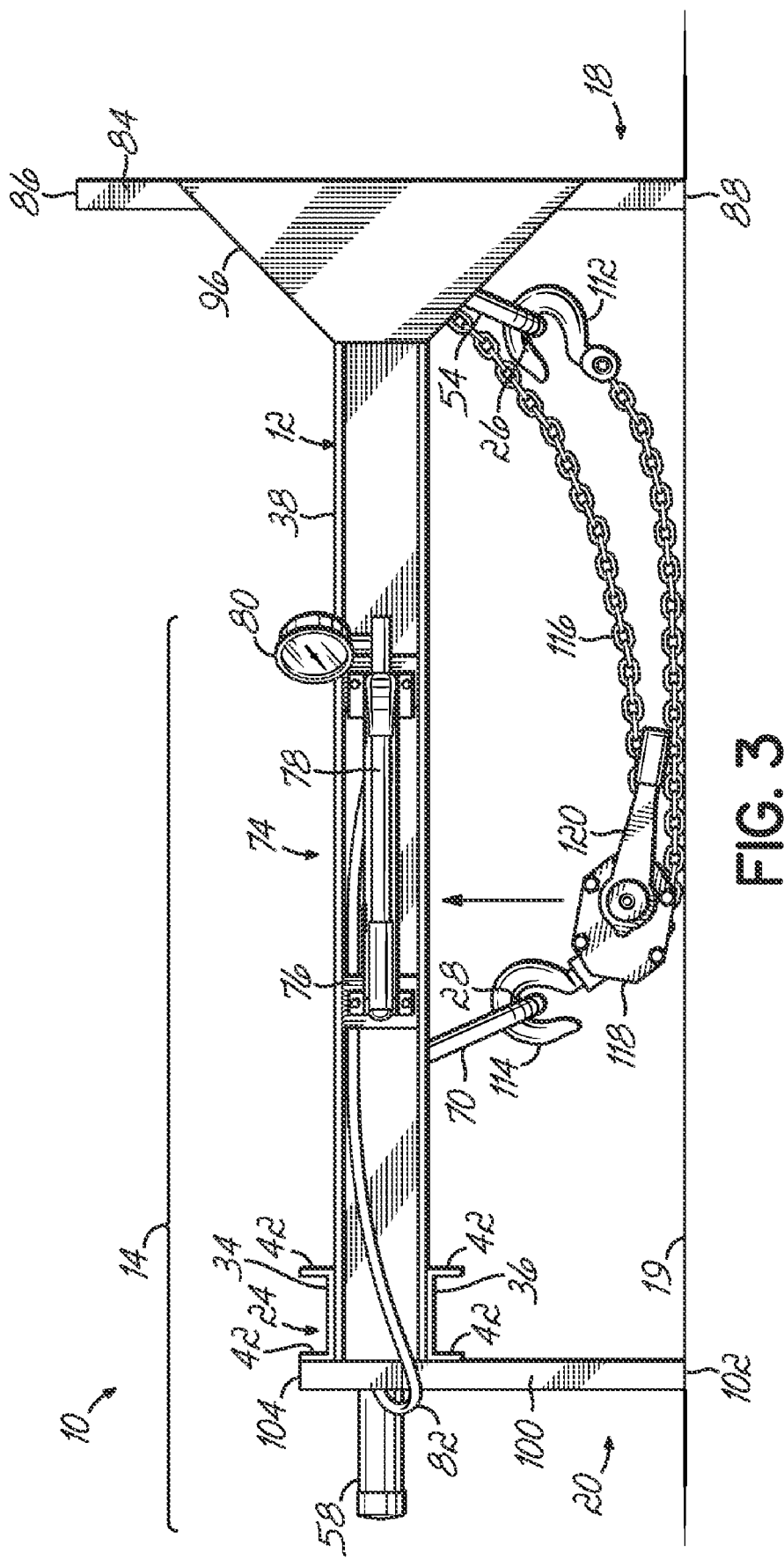
FIG. 3 is a view similar to FIG. 2 with a chain hoist at least partially resting on the ground being connected to hoist connection points.

FIG. 3 illustrates one advantage of having the test stand 10 being positioned in a horizontal orientation. A large or heavy chain hoist 16 can be placed and slid along the ground 19 and then connected to the first hoist connection point 26 and the second hoist connection point 28 that are in close reach. The chain hoist body 118 can generally remain on the ground 19 during connecting of the chain hoist 16 to the connection points 26, 28. Therefore, the amount of physical or mechanical force that needs to be used to position the chain hoist 16 for testing is lessened. After the chain hoist 16 is connected to the connection points 26, 28, the chain hoist 16 can be simply be placed into tension for testing as indicated by the arrow. Accordingly, the testing of large or heavy chain hoists 16 can be more easily facilitated.

Figure 4:
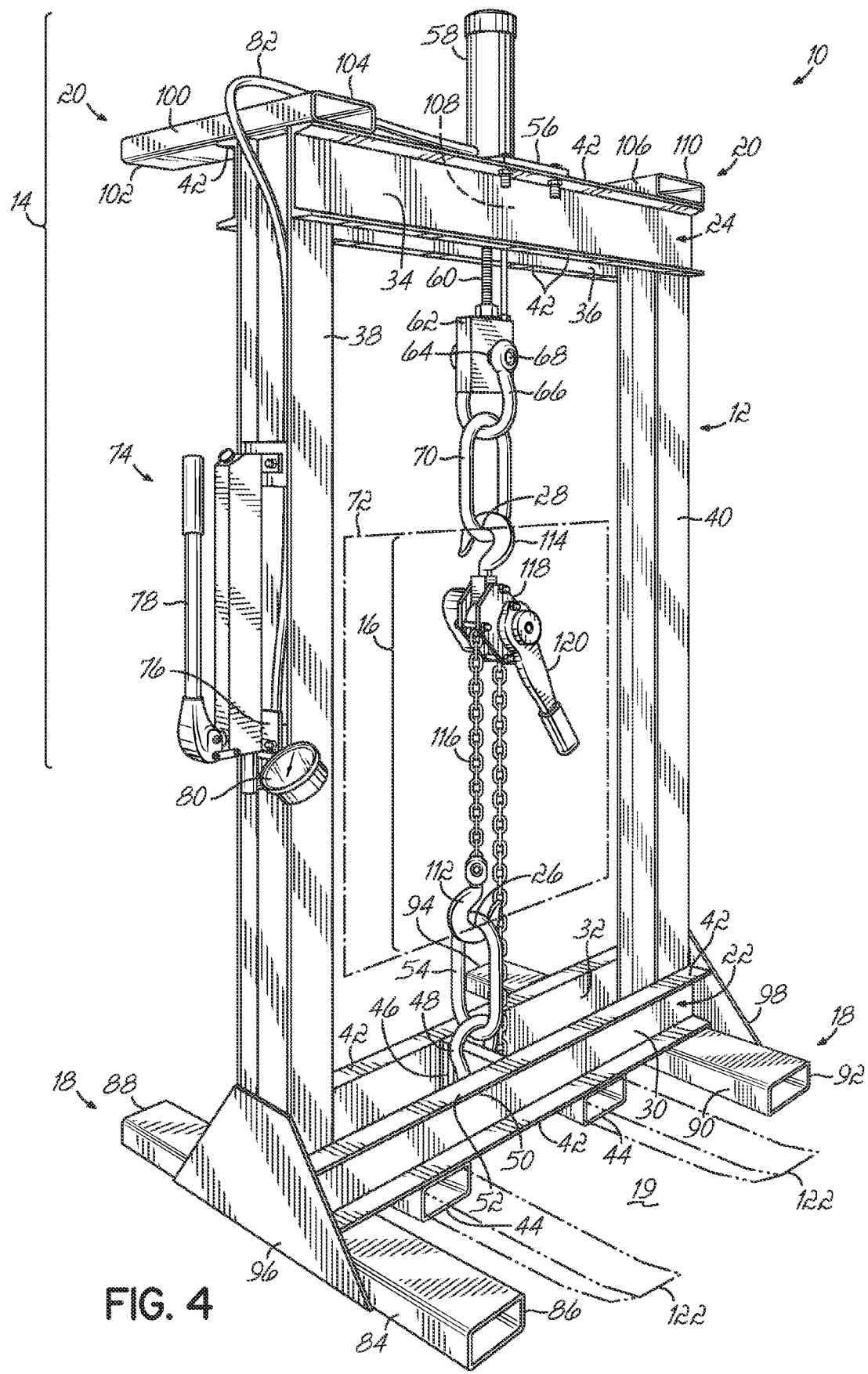
FIG. 4 is a view similar to FIG. 1 illustrating how forklift blades shown in phantom fit into the receptacles of the test stand for the purpose of explaining another aspect of the present invention.

Referring now to FIG. 4, a perspective view of the test stand 10 with forklift blades 122 shown in phantom inserted into the receptacles 44 is illustrated. If it is desired to move test stand 10, in the generally vertical orientation, in accordance with the principles of the invention, forklift blades 122 can be slid into receptacles 44 and the device lifted up and moved stably, and set down in another location. The receptacles 44 are generally tubular structures that surround the forklift blades 122 to provide a more stable connection to the test stand 10. The receptacles 44 are positioned so that the forklift blades 122 will support the test stand 10 proximate to the center of gravity of the test stand 10 to eliminate moments that cause rotation. In addition, the receptacles 44 provide a larger surface of contact between the forklift blades 122 to increase friction to prevent sliding of the test stand 10. Moreover, the tubular nature of the receptacles 44 reduces the movement of the test stand 10 if sliding or rotation in a variety of directions of the test stand 10 occurs because the forklift blades 122 will contact the receptacles 44 to resist the rotation or sliding.

In use, the test stand 10 may normally be oriented in a generally vertical orientation and a chain hoist 16 to be tested attached to connection points 26, 28 as seen in FIG. 1. The operator can then hydraulically cause the connection points 26, 28 to move apart. The movement of the connection point 28 applies a tensile load to the chain hoist 16 until the indicator dial 80 indicates that a sufficient testing force has been reached. Alternatively, the test stand 10 can be moved to a generally horizontal orientation before attaching the chain hoist 16 as illustrated in FIG. 3. The chain hoist 16 can be attached to the first hoist connection point 26 and the second hoist connection point 28 while the chain hoist body 118 is generally lying on the ground 19. At this point, the chain 116 of the chain hoist 16 is generally slack. The chain hoist 16 can then be ratcheted into a generally horizontal position to take out the slack, the movement of the second connection point 28 can also take out the slack, or some combination of the two. Once the chain hoist 16 is generally taut and lying in plane 72 the chain hoist 16 is ready for testing.

By virtue of the foregoing, there is provided a test stand that in one aspect is adapted for easy use with heavy hoists and, in another aspect, is more easily moved about but is stable during use.

While the present invention has been illustrated by the description of embodiments thereof, and while the embodiments have been described in considerable detail, it is not intended to restrict or in any way limit the scope of the appended claims to such detail. Additional advantages and modifications will readily appear to those skilled in the art. For example, while the hoist can be a chain hoist 16, other types of hoists can be tested with the invention, such as a wire rope sling, nylon sling, chain assembly, or wire and nylon chokers by way of example. Additionally, the shape of the test frame 12 could be rectangular as illustrated, square, or other shapes. The test frame 12 could be integral instead of formed from component pieces. Welding is provided as one connection method but a variety of others can be used. Other types of beams can also be used besides channels and I-beams. Similarly, other embodiments can have pairs of support members 18, 20 that are of equal lengths and affixed to the test frame 12 in a variety of positions. The connection points 26, 28 are not limited to using shackles 48, 66 and weldless endlinks 54, 70 and many other types of structures and materials can be used to connect the hoist to the test frame 12. In this regard, the term "connection points" as used herein, refers broadly to the attachment points or devices by which a chain hoist may be affixed between to relatively moveable positions for load testing. Moreover, the control of the tensioning device 14 could be automatic or, if manual, could differ from a hand pump 74 with a lever 78. The invention in its broader aspects is therefore not limited to the specific details, representative apparatus and method, and illustrative examples shown and described. Accordingly, departures may be made from such details without departing from the spirit or scope of the claims.

What is claimed is:

1. A test stand for testing a hoist including a hoist body, a chain, and two hooks said test stand comprising:

a test frame having two side members, an upper member, and a lower member, said side members spacing said upper member apart from said lower member;

a tensioning device mounted on one of said upper and lower members and operably coupled to a first connection point for attachment to a first hook of said hoist;

a second connection point attached to said other of said upper and lower members for connection to a second hook of said hoist;

a first pair of support legs attached to said test frame proximate one of said upper and lower members and for holding said test frame in a generally vertical position;

a second pair of support legs attached to said test frame proximate the other of said upper and lower members; and said second pair of support legs cooperating with said first pair of support legs for supporting said test frame in a generally horizontal orientation when said test frame is tilted over from a generally vertical position.

2. A test stand for testing hoisting and related lifting equipment in a vertical orientation or in a horizontal orientation, comprising:

a test frame including an upper member, a lower member longitudinally spaced from the upper member, a first side member, and a second side member laterally spaced from the first side member;

a tensioning system connected to the frame, the tensioning system including a hydraulic cylinder configured to apply a pulling force to, or resist a pulling force from, an item of hoisting or related lifting equipment when the item is releasably connected to the tensioning system;

a first pair of support legs connected to the test frame, the first pair of support legs configured to contact a ground surface and maintain the rest frame in a vertical orientation; and a second pair of support legs connected to the test frame, the second pair of support legs positioned above the first pair of support legs when the test frame is in a vertical orientation, the second pair of support legs in non-contacting relationship with the ground surface when the test frame is in a vertical orientation, the second pair of support legs configured to cooperate with the first pair of support legs to support the test frame in a horizontal orientation above the ground surface when the test frame is tilted over from a vertical orientation to a horizontal orientation, whereby the test frame may be used to test an item of hoisting or related lifting equipment when the test frame is in a vertical orientation and in a horizontal orientation.

3. The test stand of claim 2 wherein the hydraulic cylinder is located at the upper member, the hydraulic cylinder extending vertically upward from the upper member when the test frame is in a vertical orientation.

4. The test stand of claim 3 wherein each of the support legs is configured to contact the ground surface when the test frame is in a horizontal orientation and the ground surface is generally planar.

5. The test stand of claim 4 wherein each of the support legs includes an end that contacts the ground surface when the test frame is in a horizontal orientation and the ground surface is generally planar.

6. The test stand of claim 5 wherein the test frame defines a plane, and each of the support legs includes a portion that extends from the test frame to the end, the portion extending out from the test frame at an angle of about 90 degrees relative to the plane of the test frame.

7. The test stand of claim 6 wherein the first pair of support legs is proximate the test frame lower member, and the second pair of support legs is proximate the test frame upper member.

8. The test stand of claim 7 wherein the test frame does not pivot relative to the first pair of support legs, whereby the first pair of support legs is rotated when the test frame is tilted over from a vertical orientation to a horizontal orientation.

9. The test stand of claim 8 wherein the tensioning system includes a hydraulic hand pump fluidly connected to the hydraulic cylinder, the hydraulic hand pump located at an outwardly-facing peripheral surface of one of the test frame first and second side members in an orientation parallel to the one of the side members, whereby the hand pump is in a vertical orientation when the test frame is vertically oriented, and in a horizontal orientation when the test frame is horizontally oriented.

10. The test stand of claim 9 wherein the test stand includes a connection point connected to the hydraulic cylinder and another connection point connected to the test frame proximate the lower member, the connection points configured to releasably connect with an item of hoisting or related lifting equipment.

11. The test stand of claim 10 wherein the test stand includes a pair of elongated tubular members connected to the test frame proximate the test frame lower member, each tubular member perpendicular to the test frame and configured to releasably received a blade of a forklift.

12. The test stand of claim 2 wherein each of the support legs is configured to contact the ground surface when the test frame is in a horizontal orientation and the ground surface is generally planar.

13. The test stand of claim 2 wherein the test frame does not pivot relative to the first pair of support legs, whereby the first pair of support legs is rotated when the test frame is tilted over from a vertical orientation to a horizontal orientation.

14. The test stand of claim 2 wherein the tensioning system includes a hydraulic hand pump fluidly connected to the hydraulic cylinder, the hydraulic hand pump located at an outwardly-facing peripheral surface of one of the test frame first and second side members in an orientation parallel to the one of the side members, whereby the hand pump is in a vertical orientation when the test frame is vertically oriented, and in a horizontal orientation when the test frame is horizontally oriented.

15. The test stand of claim 2 wherein the test stand includes a connection point connected to the hydraulic cylinder and another connection point connected to the test frame proximate the lower member, the connection points configured to releasably connect with an item of hoisting or related lifting equipment.

16. The test stand of claim 2 wherein the test stand includes a pair of elongated tubular members connected to the test frame proximate the test frame lower member, each tubular member perpendicular to the test frame and configured to releasably received a blade of a forklift.

17. A test stand for testing hoisting and related lifting equipment in a vertical orientation or in a horizontal orientation, comprising:

a test frame including an upper member, a lower member longitudinally spaced from the upper member, a first side member, and a second side member laterally spaced from the first side member;

a tensioning system connected to the frame, the tensioning system including a hydraulic cylinder located at the upper member, the hydraulic cylinder extending vertically upward from the upper member when the test frame is in a vertical orientation, the hydraulic cylinder configured to apply a pulling force to, or resist a pulling force from, an item of hoisting or related lifting equipment when the item is releasably connected to the tensioning system;

a first pair of support legs connected to the test frame, the first pair of support legs configured to contact a ground surface and maintain the test frame in a vertical orientation; and a second pair of support legs connected to the test frame, the second pair of support legs positioned above the first pair of support legs when the test frame is in a vertical orientation, the second pair of support legs in non-contacting relationship with the ground surface when the test frame is in a vertical orientation, the second pair of support legs configured to cooperate with the first pair of support legs to support the test frame in a horizontal orientation above the ground surface when the test frame is tilted over from a vertical orientation to a horizontal orientation, with each of the first and second pair support legs contacting the ground surface when the ground surface is generally planar, the tensioning system further including a hydraulic band pump fluidly connected to the hydraulic cylinder, the hydraulic hand pump located at an outwardly-facing peripheral surface of one of the test frame first and second side members in an orientation parallel to the one of the side members, whereby the band pump is in a vertical orientation when the test frame is vertically oriented, and in a horizontal orientation when the test frame is horizontally oriented, whereby the test frame may be used to test an item of hoisting or related lifting equipment when the test frame is in a vertical orientation and in a horizontal orientation.

18. The test stand of claim 17 wherein each of the support legs includes an end that contacts the ground surface when the test frame is in a horizontal orientation and the ground surface is generally planar.

19. The test stand of claim 18 wherein the test frame defines a plane, and each of the support legs includes a portion that extends from the test frame to the end, the portion extending out from the test frame at an angle of about 90 degrees relative to the plane of the test frame.

20. The test stand of claim 17 wherein the first pair of support legs is proximate the test frame lower member, and the second pair of support legs is proximate the test frame upper member.

21. The test stand of claim 17 wherein the test frame does not pivot relative to the first pair of support legs, whereby the first pair of support legs is rotated when the test frame is tilted over from a vertical orientation to a horizontal orientation.

22. The test stand of claim 17 wherein the test stand includes a connection point connected to the hydraulic cylinder and another connection point connected to the test frame proximate the lower member, the connection points configured to releasably connect with an item of hoisting or related lifting equipment.

23. The test stand of claim 17 wherein the test stand includes a pair of elongated tubular members connected to the test frame proximate the test frame lower member, each tubular member perpendicular to the test frame and configured to releasably received a blade of a forklift.

* * * * *